United States Patent
Buxton et al.

[11] Patent Number: 5,709,851
[45] Date of Patent: Jan. 20, 1998

[54] PHARMACEUTICAL IODINE COMPOSITIONS WITH REDUCED IRRITANCY

[75] Inventors: Ian Richard Buxton; Stewart Thomas Leslie; Sandra Therese Antoinette Malkowska, all of Cambridge; Allan John Miller, Surrey, all of United Kingdom; Ronald Brown Miller, Basel, Switzerland; Derek Allan Prater, Cambridge, United Kingdom

[73] Assignee: Euro-Celtique, S.A., Luxembourg, Luxembourg

[21] Appl. No.: 243,534

[22] Filed: May 16, 1994

Related U.S. Application Data

[63] Continuation of Ser. No. 940,202, Sep. 1, 1992, abandoned, which is a continuation of Ser. No. 664,370, Mar. 4, 1991, abandoned.

[30] Foreign Application Priority Data

Mar. 21, 1990 [GB] United Kingdom ............... 9006346

[51] Int. Cl.$^6$ ............ A61K 31/74; A01N 25/32
[52] U.S. Cl. ............ 424/78.07; 424/78.08; 424/78.19; 424/406; 424/667; 424/668
[58] Field of Search ............ 424/405, 78.19, 424/406, 667, 668, 78.08, 78.07

[56] References Cited

U.S. PATENT DOCUMENTS

| | | | |
|---|---|---|---|
| 2,754,245 | 7/1956 | Hosmer | 424/80 |
| 2,826,532 | 3/1958 | Hosmer | 424/80 |
| 4,113,857 | 9/1978 | Shetty | 424/150 |
| 4,271,149 | 6/1981 | Winicov et al. | 424/78.25 |
| 4,320,114 | 3/1982 | Denzinger et al. | 424/78.19 |
| 4,323,557 | 4/1982 | Rosso et al. | 424/80 X |
| 4,402,937 | 9/1983 | Denzinger et al. | 424/80 |
| 4,575,491 | 3/1986 | Pollack et al. | 436/125 |
| 4,946,673 | 8/1990 | Pollack et al. | 424/80 |

FOREIGN PATENT DOCUMENTS

| | | | |
|---|---|---|---|
| 3491878 | 4/1978 | Australia | A61K 33/18 |
| 2464384 | 2/1984 | Australia | A61K 33/18 |
| 0120301 | 10/1984 | European Pat. Off. | |
| 0169320 | 1/1986 | European Pat. Off. | |
| 1580596 | 12/1980 | United Kingdom | |
| 2060385 | 5/1981 | United Kingdom | |
| 2121057 | 12/1983 | United Kingdom | C08J 3/28 |
| 8900006 | 1/1989 | WIPO | |

OTHER PUBLICATIONS

WPI Abstract No. 88–121853R.
Search Report issued on corrsponding British Application No. 9104968.4.

Primary Examiner—Neil S. Levy
Attorney, Agent, or Firm—Steinberg, Raskin & Davidson, P.C.

[57] ABSTRACT

A stable pharmaceutical composition with reduced irritancy is provided, the composition comprising an aqueous solution of elemental iodine and at least one organic substance which reacts with iodine, whereby iodine loss is controlled by providing a source of iodate ions in an amount sufficient to provide from 0.01% to 0.04% by weight iodate ions, preferably from 0.02% to 0.03% by weight iodate ions.

20 Claims, 3 Drawing Sheets

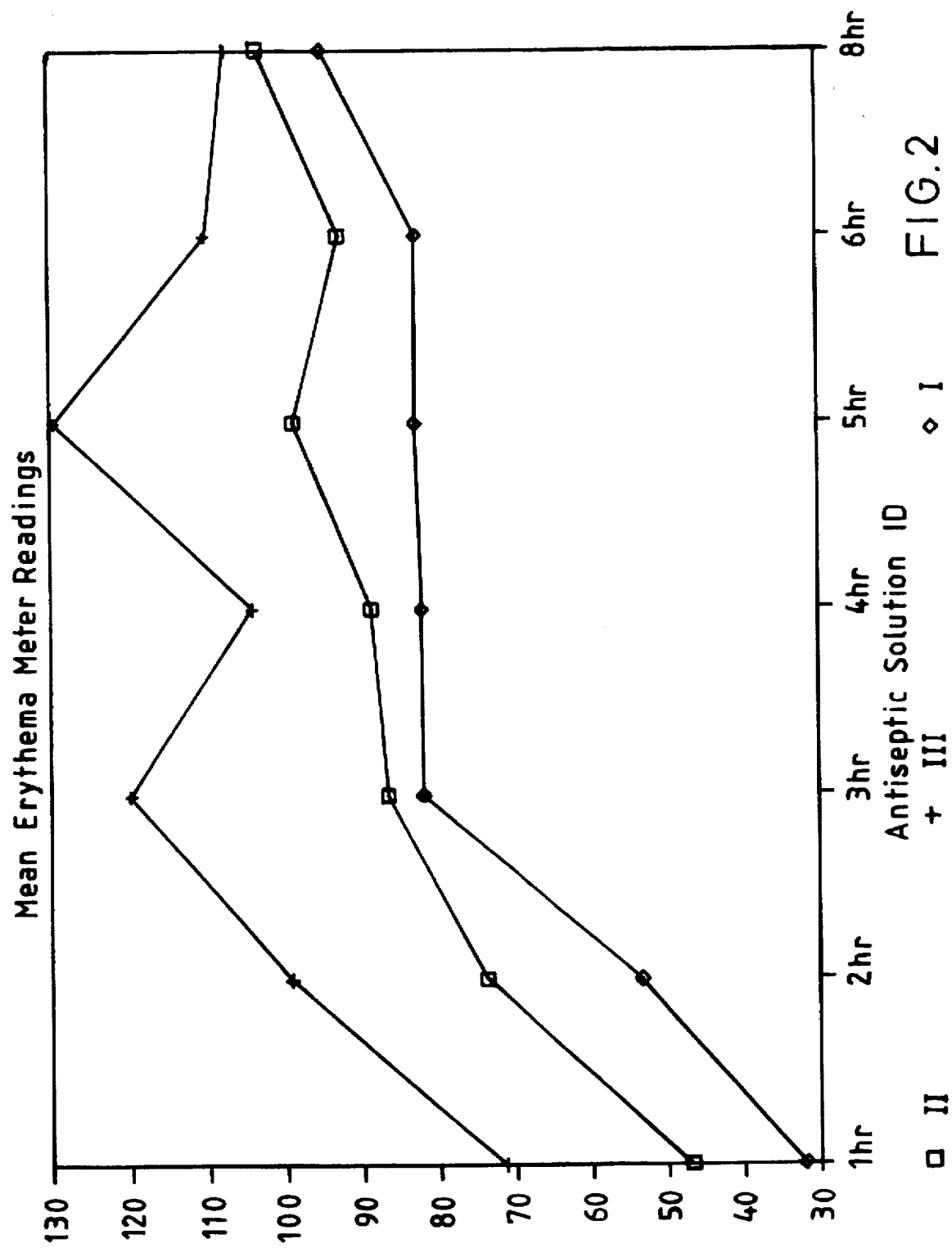

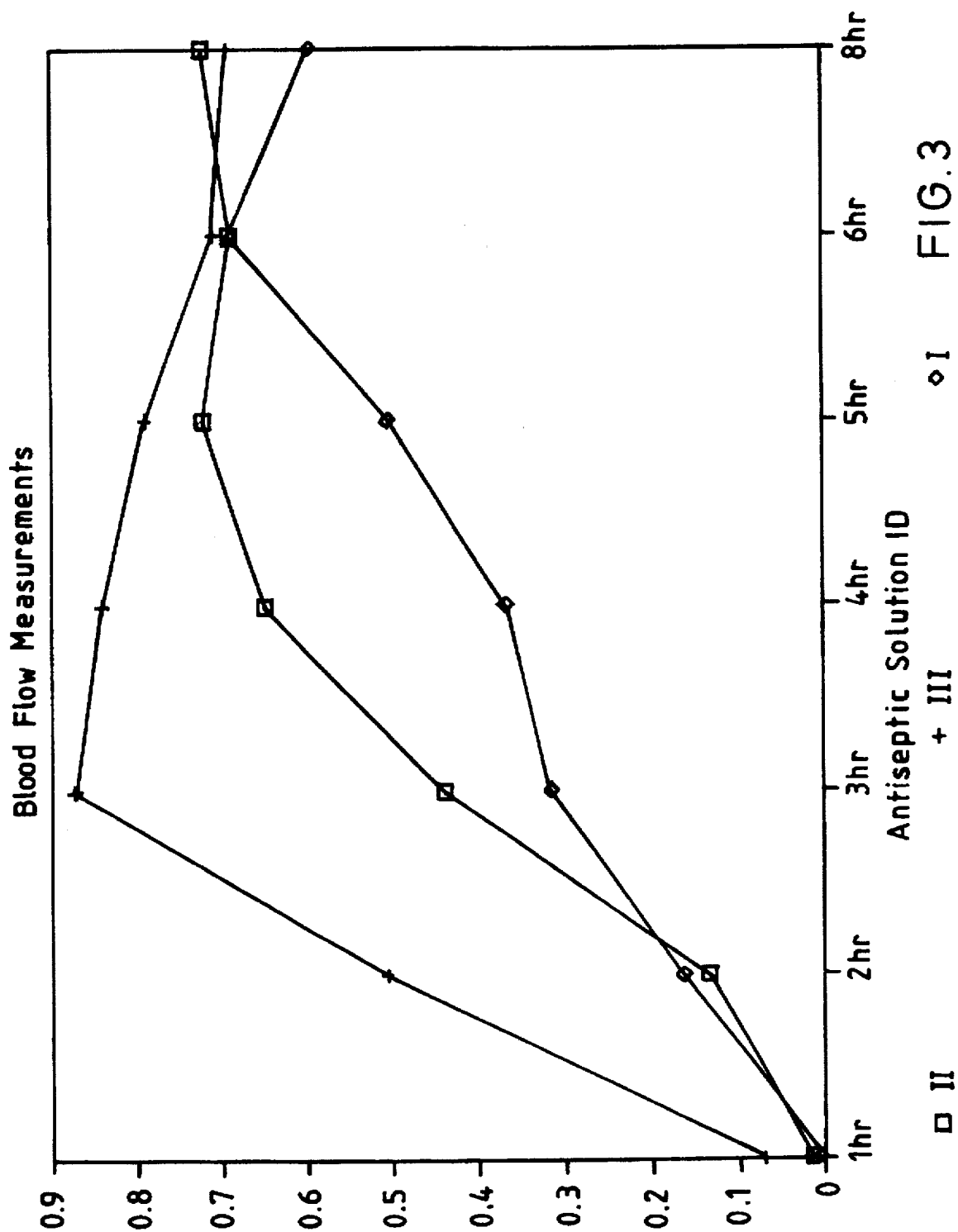

PHARMACEUTICAL IODINE COMPOSITIONS WITH REDUCED IRRITANCY

This is a continuation of application Ser. No. 07/940,202 filed on Sep. 1, 1992/now abandoned, which is a continuation of U.S. Ser. No. 07/664,370, filed Mar. 4, 1991 which is now abandoned.

BACKGROUND OF THE INVENTION

It is recognized in the art that in aqueous iodine compositions wherein the iodine is formulated with organic substances with which it reacts, such as water soluble organic solvents, iodine complexing polymers or surface active agents, the elemental iodine concentration decreases on storage leading to decreased germicidal effectiveness and lack of reproducibility of results.

One method of overcoming the problem of elemental iodine stability which has been suggested involves adding iodate or iodide ions to the aqueous solution. For example, U.K. Specification No. 2060385, describes aqueous germicidal iodine compositions comprising an aqueous solution of elemental iodine and at least one organic substance which slowly reacts with iodine wherein iodine loss on storage due to reaction with the organic substance is controlled by providing balanced sources of iodide ion in the range of about 0.025% to 0.5% and iodate ion in the range of about 0.005% to 0.2% and controlling the pH within the range of pH 5 to 7. In this way, iodine loss in the iodine composition is balanced by iodine formed from reacting iodate, iodide and hydrogen ions, the rate of formation of iodine being governed by the pH selected.

The need for stable pharmaceutical iodine compositions with less irritancy than known compositions still exists.

SUMMARY OF THE INVENTION

It is accordingly a primary object of the present invention to provide stable pharmaceutical iodine compositions with reduced irritancy.

It is another object of the present invention to provide for the method of producing such compositions and further to provide for germicidal treatment with such compositions.

Other objects and advantages of the present invention will be apparent from a further reading of the specification and of the appended claims.

Thus, the present invention relates to pharmaceutical iodine compositions, to processes for their preparation and to their medical use, and in particular, to stable germicidal iodine compositions in which the elemental iodine concentration level is maintained by the addition of iodate ions.

With the above and other objects in view, it has been found according to the present invention that stable compositions with unexpectedly reduced irritancy are obtained by adding iodate ions in the range of 0.01% to 0.04% by weight to aqueous iodine compositions.

Thus, the present invention provides a pharmaceutical composition comprising an aqueous solution of elemental iodine and at least one organic substance which reacts with iodine, whereby iodine loss is controlled by providing a source of iodate ions sufficient to provide from 0.01% to 0.04% by weight iodate ions, preferably from 0.02% to 0.03% by weight iodate ions.

Suitable organic substances for use in the present invention include those conventionally used in the art. Those include for example, water soluble solvents (such as ethanol, propanol, polyethylene glycol); iodine solubilizers; iodine complexing polymers such as polyvinylpyrrolidone or non-ionic, cationic or anionic detergent carriers or surface active agents (such as nonoxynol or sodium lauryl sulphate).

According to the invention, elemental iodine is preferably present in the range of 0.1 to 1.4% by weight, most preferably 0.75 to 1.25% by weight. Conveniently, the composition according to the invention comprises an aqueous solution of a complex of iodine with an organic iodine-complexing agent, preferably a polyvinylpyrrolidine-iodine complex. Where polyvinylpyrrolidone-iodine is used, the same is preferably present in the range of from 1% to 12% by weight to give from 0.1% to 1.4% of the available iodine in solution.

The iodate ions for use in the present invention may be obtained from any convenient source for example sodium or potassium iodate.

The pH range of compositions according to the present invention is desirably maintained within the range from pH 3 to 7, preferably pH 4 to 6. The pH is conveniently maintained in the desired range by addition of a conventional buffer such as a citrate or phosphate buffer.

Compositions according to the present invention may be formulated for administration by any convenient route conventional in the art. Such compositions are preferably in a form adapted for use in medicine, in particular human medicine, and can conveniently be formulated in conventional manner using one or more pharmaceutically acceptable carriers or excipients. Compositions according to the present invention are conveniently formulated for topical or mucosal administration in the form of solutions, soaps, ointments, gels or paints.

In a further aspect there is provided a process for preparing a pharmaceutical iodine composition according to the invention, comprising forming a solution of iodine and at least one organic substance with which iodine reacts and adding iodate ions in the range of from 0.01% to 0.04% by weight.

In an alternative aspect, there is provided a method for the germicidal treatment of a mammal, including man, comprising administering a composition as defined above. It will be appreciated that reference to treatment is intended to include phophylaxis.

BRIEF DESCRIPTION OF THE DRAWINGS

The present invention is further illustrated in connection with the accompanying drawings in which:

FIG. 2 is a graphical representation of mean erythema meter readings, and

FIG. 3 is a graphical representation of blood flow measurements, all in connection with tests with respect to the compositions of the present invention.

DESCRIPTION OF PREFERRED EMBODIMENTS

Figure 1:
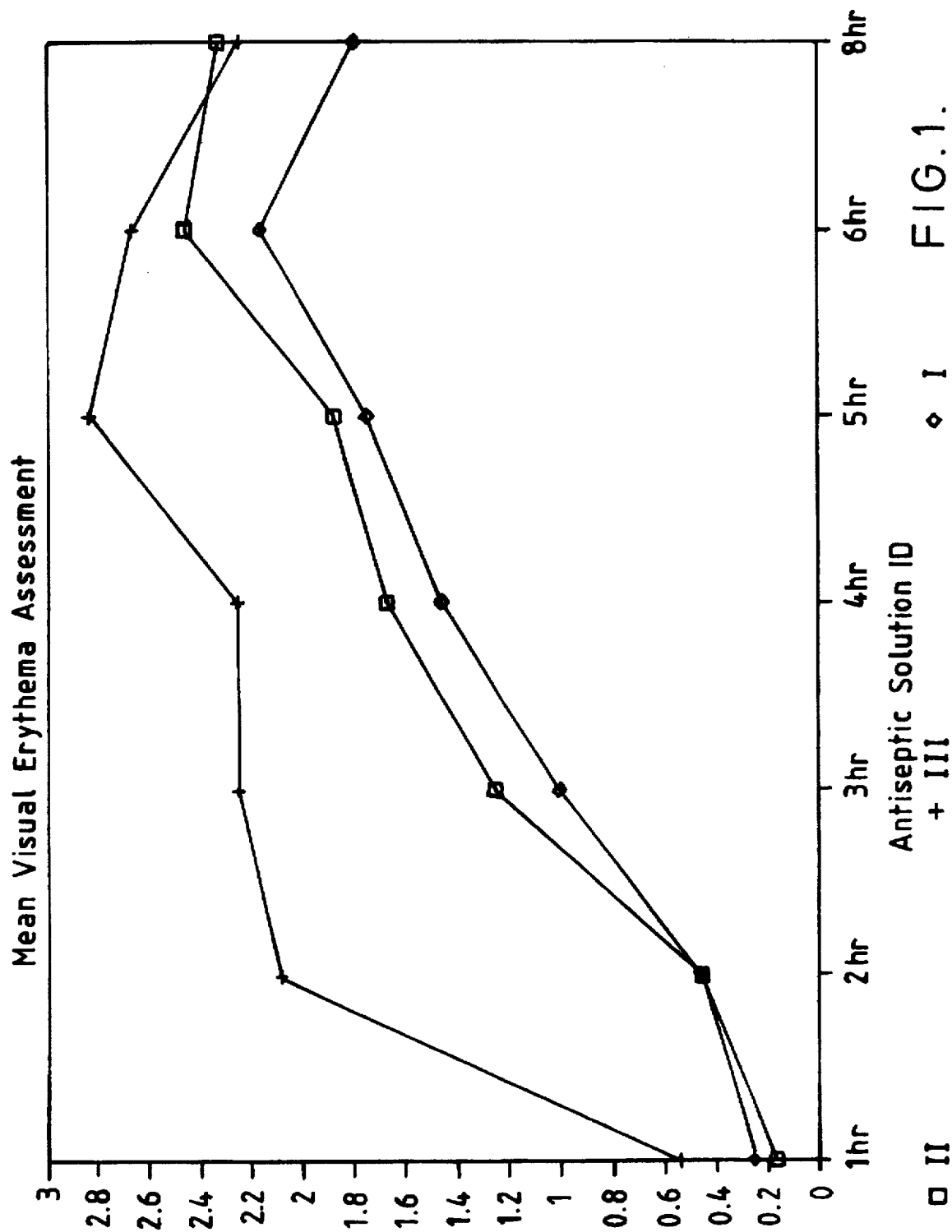
FIG. 1 is a graphical representation of mean visual erythema assessment.

The following example is given to further illustrate the present invention. The scope of the invention is not, however, meant to be limited to the specific details thereof.

EXAMPLE

The following iodine compositions were prepared.

| Constituents | I % w/w | II (Comparative) % w/w | III (Comparative) % w/w |
|---|---|---|---|
| Povidone-iodine | 10.00 | 10.00 | 10.00 |
| (Overage %) | (0) | (20) | (0) |
| Glycerol | 1.0 | 1.0 | 1.0 |
| Nonoxynol 9 | 0.25 | 0.25 | 0.25 |
| Potassium iodate | 0.03 | — | 0.225 |
| Citrate/phosphate Buffer (Approx. | 1.11 | 0.20 | 1.1 |
| Sodium hydroxide | q.s. | q.s. | q.s. |
| Purified water | to 100.00 | to 100.00 | to 100.00 |

A portion of the purified water (60%) was placed in a suitable vessel. Glycerol was added and mixed until the solution was uniform. Povidone-iodine was mixed until dissolved. Potassium iodate was dissolved in a separate small quantity of purified water and added to the povidone-iodine solution. The citrate phosphate were dissolved in water and added to the solution with mixing following by the addition of Nonoxynol 9. The solution was made up with the remaining purified water and the pH adjusted to within the desired range.

The cutaneous irritancy of the three compositions was assessed in a panel of 12 normal volunteer subjects.

Each subject received 7 applications of each material under occlusive patches to separate sites on the back. The treatments were applied to 21 sites on the lower and upper parts of the back using 12 mm aluminum Finn chambers on Scanpor tape with filter paper inserts. 50 mol of the solution was pipetted onto the filter paper. The chamber and filter paper was then applied to one of the sites on the back and the procedure repeated for all 21 sites.

One chamber per treatment was removed after 1, 2, 3, 4, 5, 6 and 8 hours following application and the skin assessed. Assessments were performed 30 minutes after removal of the chambers to allow for any erythema due to chamber removal to subside.

Following removal of the chambers, irritancy was assessed using three procedures.

Sites were assessed for erythema/oedema using the following categorical scale:

0 - No reaction
0.5 - Slight patch erythema
1 - Slight uniform erythema
2 - Moderate erythema
3 - Strong erythema
4 - Strong erythema, spreading outside patch
5 - Strong erythema, spreading outside patch with either swelling or vesiculation
6 - Severe reaction with erosion When at any time point a site was scored at Grade 3 (strong erythema) or more, then the applications were removed from all remaining sites of that solution on that subject. In this situation, the sites were assessed at the same time points as originally scheduled as if no severe reactions had occurred.

Erythema was also assessed using an Erythema Meter.

Cutaneous blood flow was measured using a Laser Doppler blood flow device (periflux blood flow meter, Perimed, Sweden).

METHOD OF ANALYSIS

In the clinical study the data was either non-parametric in nature or not normally distributed or not of equal variances. Therefore, it was decided that a non-parametric method of analysis was the most suitable.

As the data is based on within subject comparison (each subject receiving all three treatments) the Friedman non-parametric analysis of variance was considered appropriate. Comparisons were made between treatments at t=1, t=2, t=3 and t=4 hours for the three parameters measured.

If a significant value for the test statistic was found, then a multiple comparison procedure was carried out in order to determine individual treatment difference. The threshold value for significance was set at 5%.

Analysis was not carried out at the later time points as in some subjects the treatments had been removed.

RESULTS

The results (means and standard deviations) for visual erythema assessment, erythema meter readings and blood flow measurements are shown in FIGS. 1-3.

The results for all three methods of assessment show a clear difference in the irritancy potential of the three solutions. From the results it can be seen that composition III is the most irritant, producing the greatest rate of increase of parameters assessed as well as the highest mean value. Composition II produced the second highest values while composition I produced the least irritancy. Statistical analysis confirmed these differences at the 2, 3 and 4 hour time points. It will be appreciated that these time periods are important in the clinical situation of an operation.

An in-vitro study to compare the bactericidal activity of solutions I, II and III using standard microbiological dilution techniques against a test bacterial organism, Staphylococcus aureus NCTC 29213 showed no difference in the bactericidal activity of the three solutions.

While the invention has been illustrated with respect to particular compositions, it is apparent that variations and modifications of the invention can be made within departing from the spirit or scope of the invention.

What is claimed is:

1. Method of preparing a stable pharmaceutical aqueous iodine composition which upon application is substantially non-irritating, which comprises forming an aqueous solution containing an amount of about 0.1 to about 1.4% of elemental iodine by weight of the composition and at least one organic substance selected from the group consisting of iodine solubilizers; iodine complexing polymers, non-ionic surface active agents, cationic surface active agents and artionic surface active agents; adding iodate ions in an amount such that the resulting composition contains from about 0.01% to about and not more that 0.04% iodate ions by weight of said composition, said iodate ions controlling loss of elemental iodine in said composition due to a reaction with said organic substance to maintain the germicidal effective amount of elemental iodine, and providing the resulting composition with a pH of from about 3 to about 7, such that said resulting composition provides germicidal action without substantially irritating skin or mucosa when applied topically to an affected area of skin or mucosa.

2. Method according to claim 1 wherein the amount of iodate ions is within the range of 0.02% to 0.03% by weight.

3. Method according to claim i wherein the amount of elemental iodine is within the range of 0.75 to 1.25% by weight.

4. Method according to claim 1 wherein the organic substance is polyvinylpyrrolidone.

5. Method according to claim 6 wherein the amount of polyvinylpyrrolidone is within the range of 1% to 12% by weight.

6. The method of claim 1, wherein said iodate ions are derived from potassium iodate.

7. The method of claim 1, further comprising adding a buffer to said composition.

8. The method of claim 7, wherein a sufficient amount of buffer is added to adjust the pH of said composition to from about 4 to about 6.

9. A stable pharmaceutical aqueous iodine composition which upon application is substantially non-irritating, which comprises an aqueous solution containing an amount of about 0.1 to about 1.4% of elemental iodine by weight of the composition and at least one organic substance selected from the group consisting of iodine solubilizers, iodine complexing polymers, non-ionic surface active agents, cationic surface active agents and anionic surface active agents; and iodate ions in an amount such that the resulting composition contains from about 0.01% to about and not more that 0.4% iodate ions by weight of the composition, said iodate ions controlling loss of elemental iodine in said composition due to a reaction with said organic substance to maintain the germicidal effective amount of elemental iodine, said composition having a pH of from about 3 to about 7 and providing germicidal action without substantially irritating skin or mucosa when applied topically to an affected area of skin or mucosa.

10. The aqueous iodine composition of claim 9, wherein said organic substance is polyvinylpyrrolidone.

11. The aqueous iodine composition of claim 10, wherein said polyvinylpyrrolidone is present in an amount of from 1 to 12% by weight of the composition.

12. The aqueous iodine composition of claim 9, further comprising a buffer.

13. The aqueous iodine composition of claim 9, further comprising a buffer.

14. The aqueous iodine composition of claim 13, wherein the pH of the final composition is from about 4 to about 6.

15. A method of substantially reducing skin irritancy caused by application of iodine preparations to the human skin comprising the steps of preparing an aqueous iodine preparation in accordance with claim 1; and applying a germicidally effective amount of said preparation to the human skin.

16. The method of claim 15, wherein said organic substance is polyvinylpyrrolidone.

17. A method of degerming the skin of a human, comprising applying a germicidally effective amount of the aqueous iodine composition of claim 9 to the skin of a human.

18. The composition of claim 9, wherein said iodate ions are derived from a salt selected from the group consisting of sodium iodate and potassium iodate.

19. The composition of claim 18, wherein the pH of said composition is in the range of from 4to 6.

20. The method of claim 1, further comprising adjusting the pH of said composition to between pH 4 and 6.

* * * * *